United States Patent [19]
Madsen et al.

[11] Patent Number: 5,962,449
[45] Date of Patent: Oct. 5, 1999

[54] TRICYCLIC COMPOUNDS IN TREATING HYPERALGESIC CONDITIONS AND NIDDM

[75] Inventors: Peter Madsen, Bagsvaerd; Knud Erik Andersen, Smørum; Rolf Hohlweg, Kvistgaard; Florenzio Zaragossa Dörwald; Tine Krogh Jørgensen, both of Herlev; Uffe Bang Olsen, Vallensbaek; Henrik Sune Andersen, København Ø, all of Denmark

[73] Assignee: Novo Nordisk A/S, Bagsvaerd, Denmark

[21] Appl. No.: 08/623,447

[22] Filed: Mar. 28, 1996

[30] Foreign Application Priority Data

Apr. 7, 1995 [DK] Denmark ................. 0407/95
Sep. 11, 1995 [DK] Denmark ................. 1002/95

[51] Int. Cl.$^6$ ............ A01N 43/46; C07D 487/00; C07D 265/34; C07D 221/06
[52] U.S. Cl. .............. 514/217; 514/213; 514/224.5; 514/229.8; 514/250; 514/290; 540/522; 540/547; 540/557; 544/101; 544/349; 546/79
[58] Field of Search .............. 514/213, 229.8, 514/224.5, 250, 290, 217; 540/547, 557, 522; 544/101, 349; 546/79

[56] References Cited

U.S. PATENT DOCUMENTS 2,860,137 11/1958 Cusic et al. .................. 260/243
5,256,409 10/1993 Blincko .................. 424/85.8

FOREIGN PATENT DOCUMENTS 0 508 334 10/1992 European Pat. Off. .
0 589 038 3/1994 European Pat. Off. .
1084266 6/1960 Germany .
1134589 11/1968 United Kingdom .

OTHER PUBLICATIONS

Adamczyk et. al., "A Facile Synthetic Route to Hydroxy...", Org. Prep. & Proc. Int., vol. 23(3), 1991, pp. 365–372.

Berkow et. al., "The Merck Manual of Diagnosis and Therapy," 16$^{th}$ Edition, 1992, pp. 1418–1419.

Adamczyk et. al., "Characterization of Protein–Hapten Conjugates..." Bioconjugate Chem. vol.5(6), 1994, pp. 631–635.

*Primary Examiner*—Richard L. Raymond
*Assistant Examiner*—Tamthom N. Truong
*Attorney, Agent, or Firm*—Steve T. Zelson; Carol E. Rozek

[57] ABSTRACT

The present invention relates to novel N-substituted amino acids and esters thereof in which a substituted alkyl chain forms part of the N-substituent or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation.

8 Claims, No Drawings

TRICYCLIC COMPOUNDS IN TREATING HYPERALGESIC CONDITIONS AND NIDDM

FIELD OF THE INVENTION

The present invention relates to novel N-substituted amino acids and esters thereof in which a substituted alkyl chain forms part of the N-substituent or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation. The invention also relates to the use of the present compounds for the treatment of insulin resistance in non-insulin-dependent diabetes mellitus (NIDDM) or aging, the present compounds knowing to interfere with neuropeptide containing C-fibres and hence inhibit the secretion and circulation of insulin antagonizing peptides like CGRP or amylin.

BACKGROUND OF THE INVENTION

The nervous system exerts a profound effect on the inflammatory response. Antidromic stimulation of sensory nerves results in localized vasodilation and increased vascular permeability (Janecso et al. Br. J. Pharmacol. 1967, 31, 138–151) and a similar response is observed following injection of peptides known to be present in sensory nerves. From this and other data it is postulated that peptides released from sensory nerve endings mediate many inflammatory responses in tissues like skin, joint, urinary tract, eye, meninges, gastro-intestinal and respiratory tracts. Hence inhibition of sensory nerve peptide release and/or activity, may be useful in treatment of, for example arthritis, dermatitis, rhinitis, asthma, cystitis, gingivitis, thrombophlelitis, glaucoma, gastrointestinal diseases or migraine.

Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1–E10, 1993). This peptide may represent an important physiological modulator of intracellular glucose trafficking in physiological conditions, such as exercise, and may also contribute to the decreased insulin action and skeletal muscle glycogen synthase in pathophysiological conditions like NIDDM or aging-associated obesity (Melnyk et al. Obesity Res. 3, 337–344, 1995) where circulating plasma levels of CGRP are markedly increased. Hence inhibition of release and/or activity of the neuropeptide CGRP may be useful in the treatment of insulin resistance related to type 2 diabetes or aging.

In U.S. Pat. Nos. 4,383,999 and 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as GABA uptake inhibitors. EP 221572 claims that 1-aryloxyalkylpyridine-3-carboxylic acids are inhibitors of GABA uptake.

DESCRIPTION OF THE INVENTION

The present invention relates to novel N-substituted amino acids and esters thereof of formula I

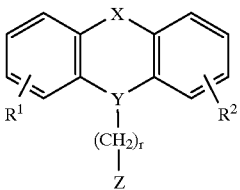

(I)

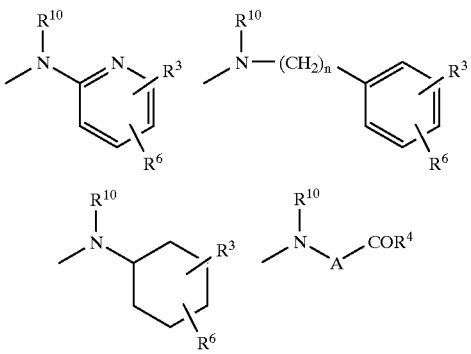

wherein

R$^1$ and R$^2$ independently are hydrogen, halogen, trifluoromethyl, hydroxy, C$_{1-6}$-alkyl or C$_{1-6}$-alkoxy; and Y is >N—CH$_2$—, >CH—CH$_2$— or >C=CH— wherein only the underscored atom participates in the ring system; and X is —O—, —S—, —C(R$^6$R$^7$)—, —CH$_2$CH$_2$—, —CH=CH—CH$_2$—, —CH$_2$—CH=CH—, —CH$_2$—(C=O)—, —(C=O)—CH$_2$—, —CH$_2$CH$_2$CH$_2$—, —CH=CH—, —N(R$^8$)—(C=O)—, —(C=O)—N(R$^8$)—, —O—CH$_2$—, —CH$_2$—O—, —S—CH$_2$—, —CH$_2$—S—, —(C=O)—, —N(R$^9$)— or —(S=O)— wherein R$^6$, R$^7$, R$^8$ and R$^9$ independently are hydrogen or C$_{1-6}$-alkyl; and r is 1, 2 or 3; and Z is selected from wherein n is 0 or 1; and R$^3$ is —(CH$_2$)$_m$OH or —(CH$_2$)$_s$COR$^4$ wherein m is 0, 1, 2, 3, 4, 5 or 6 and s is 0 or 1 and wherein R$^4$ is —OH, —NH$_2$, —NHOH or C$_{1-6}$-alkoxy; and R$^5$ is hydrogen, halogen, trifluoromethyl, hydroxy, C$_{1-6}$-alkyl or C$_{1-6}$-alkoxy; and R$^{10}$ is hydrogen or C$_{1-6}$-alkyl;

A is C$_{1-6}$-alkylene, C$_{2-6}$-alkenylene or C$_{2-6}$-alkynylene; or a pharmaceutically acceptable salt thereof.

The compounds of formula I may exist as geometric and optical isomers and all isomers and mixtures thereof are included herein. Isomers may be separated by means of standard methods such as chromatographic techniques or fractional crystallization of suitable salts.

Preferably, the compounds of formula I exist as the individual geometric or optical isomers.

The compounds according to the invention may optionally exist as pharmaceutically acceptable acid addition salts or—when the carboxylic acid group is not esterified—as pharmaceutically acceptable metal salts or—optionally alkylated—ammonium salts.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts, and include the pharmaceutically acceptable salts listed in Journal of Pharmaceutical Science, 66, 2 (1977) which are hereby incorporated by reference.

The term "$C_{1-6}$-alkyl" as used herein, alone or in combination, refers to a straight or branched, saturated hydrocarbon chain having 1 to 6 carbon atoms such as e.g. methyl, ethyl, n-propyl, isopropyl, n-butyl, sec-butyl, isobutyl, tert-butyl, n-pentyl, 2-methylbutyl, 3-methylbutyl, n-hexyl, 4-methylpentyl, neopentyl, n-hexyl, 1,2-dimethylpropyl, 2,2-dimethylpropyl and 1,2,2-trimethylpropyl.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "halogen" means fluorine, chlorine, bromine or iodine.

Illustrative examples of compounds encompassed by the present invention include:

3-(N-Methyl-N-(3-(10,11-dihydrodibenzo[a,d]cyclohepten-5-ylidene)-1-propyl)amino)propionic acid;
4-(N-Methyl-N-(3-(10,11-dihydrodibenzo[a,d]cyclohepten-5-ylidene)-1-propyl)amino)butyric acid;
3((3-(10,11-Dihydro-5H-dibenz[b,f]azepin-5-yl)-1-propyl)amino)propionic acid;
2-(N-(3-(10,11-Dihydro-5H-dibenz[b,f]azepin-5-yl)-1-propyl)-N-methylamino)succinic acid;
2-((3-(10,11-Dihydro-5H-dibenz[b,f]azepin-5-yl)-1-propyl)amino)benzoic acid;
4-(N-(3-(10,11-Dihydro-5H-dibenz[b,f]azepin-5-yl)-1-propyl)-N-methylamino)-1-methyl-3-piperidinecarboxylic acid;
2-(N-(3-(10,11-Dihydro-5H-dibenz[b,f]azepin-5-yl)-1-propyl)-N-methylamino)nicotinic acid;
2-((N-(3-(10,11-Dihydro-5H-dibenz[b,f]azepin-5-yl)-1-propyl)-N-methylamino)methyl)benzoic acid;
2-(N-(3-(10,11-Dihydro-5H-dibenz[b,f]azepin-5-yl)-1-propyl)-N-methylamino)-1-cyclohexanecarboxylic acid;
2-(3-(10,11-Dihydro-5H-dibenz[b,f]azepin-5-yl)-1-propylamino)pyridin-3-ol;
3-((3-(10,11-Dihydro-5H-dibenz[b,f]azepin-5-yl)-1-propyl)amino)benzoic acid;
2-((3-(10,11-Dihydro-5H-dibenzo[a,d]cyclohepten-5-ylidene)-1-propyl)amino)-benzoic acid;
2-(N-(3-(3-Chloro-10,11-dihydro-5H-dibenz[b,f]azepin-5-yl)-1-propyl)amino)-benzoic acid;
5-Bromo-2-(N-(3-(10,11-dihydro-5H-dibenzo[a,d]cyclohepten-5-ylidene)-1-propyl)amino)benzoic acid;
or a pharmaceutically acceptable salt thereof.

As used herein, the term "patient" includes any mammal which could benefit from treatment of neurogenic pain or inflammation or insulin resistance in NIDDM. The term particularly refers to a human patient, but is not intended to be so limited.

It has been demonstrated that the novel compounds of formula I inhibit neurogenic inflammation which involves the release of neuropeptides from peripheral and central endings of sensory C-fibres. Experimentally this can be demonstrated in animal models of formalin induced pain or paw oedema (Wheeler and Cowan, Agents Actions 1991, 34, 264–269) in which the novel compounds of formula I exhibit a potent inhibitory effect. Compounds of formula I may be used to treat all painful, hyperalgesic and/or inflammatory conditions in which C-fibers play a pathophysiological role by eliciting neurogenic pain or inflammation, i.e.: Acutely painful conditions exemplified by migraine, post-operative pain, burns, bruises, post-herpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, chronic pancreatitis, inflammatory skin disease including psoriasis and autoimmune dermatoses, osteoporotic pain.

Further, it has been demonstrated that the compounds of general formula I improves the glucose tolerance in diabetic ob/ob mice and that this may result from the reduced release of CGRP from peripheral nervous endings. Hence the compounds of general formula I may be used in the treatment of NIDDM as well as aging-associated obesity. Experimentally this has been demonstrated by the subcutaneous administration of glucose into ob/ob mice with or without previous oral treatment with a compound of general formula I.

The compounds of formula I may be prepared by the following method:

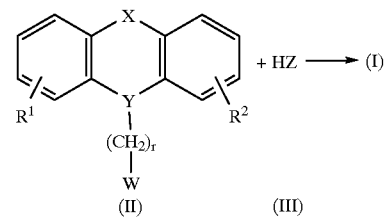

A compound of formula II wherein $R^1$, $R^2$, X, Y and r are as defined above and W is a suitable leaving group such as halogen, p-toluene sulphonate or mesylate may be reacted with an amino compound of formula III wherein Z is as defined above. This alkylation reaction may be carried out in a solvent such as acetone, dibutylether, 2-butanone, methyl ethyl ketone, ethyl acetate, tetrahydrofuran (THF) or toluene in the presence of a base e.g. sodium hydride and a catalyst, e.g. an alkali metal iodide at a temperature up to reflux temperature for the solvent used for e.g. 1 to 120 h. If esters have been prepared in which $R^4$ is alkoxy, compounds of formula I wherein $R^4$ is OH may be prepared by hydrolysis of the ester group, preferably at room temperature in a mixture of an aqueous alkali metal hydroxide solution and an alcohol such as methanol or ethanol, for example, for about 0.5 to 6 h.

Compounds of formula II and III may readily be prepared by methods familiar to those skilled in the art.

Under certain circumstances it may be necessary to protect the intermediates used in the above methods e.g. a compound of formula III with suitable protecting groups. The carboxylic acid group can, for example, be esterified. Introduction and removal of such groups is described in "Protective Groups in Organic Chemistry" J. F. W. McOrnie ed. (New York, 1973).

PHARMACOLOGICAL METHODS

Formalin induced pain or paw oedema

Values for in vivo inhibition of formalin induced pain or oedema for the compounds of the present invention were assessed in mice essentially by the method of Wheeler-Aceto and Cowan (Agents Action 1991, 34, 265–269).

About 20 g NMRI female mice were injected 20 μl 1% formalin into the left hind paw. The animals were then placed on a heated (31° C.) table, and the pain response was scored. After 1 h they were killed and bled. Left and right hind paws were removed and the weight difference between the paws was used as indication of the oedema response of the formalin injected paw.

Reduced release of CGRP ob/ob female mice, 16 weeks of age, where injected glucose (2 g/kg) subcutaneously. At times hereafter blood glucose was determined in tail venous blood by the glucose oxidase method. At the end of the study the animals were decapitated and trunck blood collected. Immunoreactive CGRP was determined in plasma by radio-immuno-assay. Two groups of animals were used. The one group was vehicle treated, whereas the other group received a compound of formula I via drinking water (100 mg/l) for five days before the test.

Values for inhibition of formalin induced pain response for some representative compounds are recorded in table 1.

TABLE 1

Inhibition of formalin induced pain response at 0.1 mg/kg

| Example no. | % Pain inhibition |
| --- | --- |
| 1 | 35 |
| 2 | 36 |
| 3 | 16 |
| 4 | 12 |
| 5 | 30 |

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

The compounds of formula I may be administered in a pharmaceutically acceptable acid addition salt form or where possible as a metal or a lower alkylammonium salt. Such salt forms exhibit approximately the same order of activity as the free base forms.

This invention also relates to pharmaceutical compositions comprising a compound of formula I or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatin, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

Generally, the compounds of this invention are dispensed in unit dosage form comprising 50–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet which may be prepared by conventional tabletting techniques contains

| Core: | |
| --- | --- |
| Active compound (as free compound or salt thereof) | 100 mg |
| Colloidal silicon dioxide (Areosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating: | |
| HPMC approx. | 9 mg |
| *Mywacett ® 9-40 T approx. | 0.9 mg |

*Acylated monoglyceride used as plasticizer for film coating.

The route of administration may be any route which effectively transports the active compound to the appropriate or desired site of action, such as oral or parenteral e.g. rectal, transdermal, subcutaneous, intranasal, intramuscular, topical, intravenous, intraurethral, ophthalmic solution or an ointment, the oral route being preferred.

EXAMPLES

The process for preparing compounds of formula I and preparations containing them is further illustrated in the following examples, which, however, are not to be construed as limiting.

Hereinafter, TLC is thin layer chromatography, CDCl$_3$ is deuterio chloroform and DMSO-d$_6$ is hexadeuterio dimethylsulfoxide. The structures of the compounds are confirmed by either elemental analysis or NMR, where peaks assigned to characteristic protons in the title compounds are presented where appropriate. $^1$H NMR shifts ($\delta_H$) are given in parts per million (ppm). M.p. is melting point and is given in °C. and is not corrected. Column chromatography was carried out using the technique described by W. C. Still et al, J. Org. Chem. (1978), 43, 2923–2925 on Merck silica gel 60 (Art. 9385). Compounds used as starting materials are either known compounds or compounds which can readily be prepared by methods known per se.

Example 1

2-((3-(10,11-Dihydro-5H-dibenz[b,f]azepin-5-yl)-1-propyl)amino)benzoic Acid

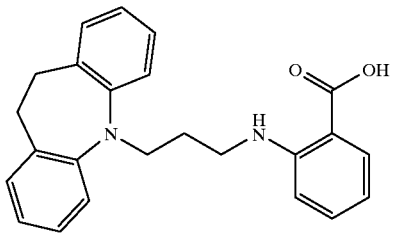

To a suspension of 10,11-dihydro-5H-dibenz[b,f]azepine (27.6 g, 0.141 mol) in toluene (250 ml), ethyl malonyl chloride (25.0 g, 0.166 mol) was added and the resulting mixture was heated at reflux temperature for 1 h. Saturated aqueous sodium bicarbonate (200 ml) was added and the phases were separated. The organic phase was washed with brine (2×150 ml), dried ($MgSO_4$) and concentrated in vacuo. This afforded 56.0 g of 3-(10,11-dihydro-5H-dibenz[b,f]azepin-5-yl)-3-oxopropionic acid ethyl ester in quantitative yield as an oil, which was used in the following step without further purification.

Lithium aluminium hydride (20.0 g, 0.527 mol) was suspended in toluene (800 ml) and tetrahydrofuran (80 ml) was added. The resulting suspension was cooled to 10–20° C., and the above amide (0.141 mol), dissolved in tetrahydrofuran (250 ml), was added dropwise keeping the temperature at 10–20° C. When addition was complete the resulting mixture was stirred at room temperature overnight. Under cooling, 2N sodium hydroxide (200 ml) was carefully added followed by water (1.0 l). The organic layer was decanted off and the aqueous phase was extracted with toluene (2×300 ml). The combined organic extracts were washed with brine (2×100 ml), dried ($MgSO_4$) and concentrated in vacuo. The residue was purified by flash chromatography on silica gel (175 g) using a gradient of heptane and ethyl acetate (10:0→2:1). This afforded 21.2 g (59%) of 3-(10,11-dihydro-5H-dibenz[b,f]azepin-5-yl)-1-propanol as an oil.

TLC: $R_f$=0.55 ($SiO_2$: ethyl acetate/heptane=1:1).

The above alcohol (1.17 g, 0.00462 mol) was dissolved in toluene (30 ml) at 0° C. and triethylamine (1.18 g, 0.0117 mol) and methanesulfonyl chloride (0.70 ml, 0.009 mol) were added. After stirring for 1 h at 0° C., water (50 ml) was added. The phases were separated, the organic phase was washed with brine (20 ml), dried ($MgSO_4$), and concentrated in vacuo. The resulting crude mesylate was mixed with 2-aminobenzoic acid ethyl ester (5.00 ml, 0.034 mol) and the resulting mixture was heated at 110° C. for 16 h. Water (50 ml) was added, and the mixture was extracted with ethyl acetate (2×20 ml). The combined organic phases were washed with brine (20 ml), dried ($MgSO_4$) and concentrated in vacuo. The residue was purified by flash chromatography on silica gel (75 g) using a gradient of heptane and ethyl acetate (10:0→10:2), to give 2.60 g of a mixture of starting material and 2-((3-(10,11-dihydro-5H-dibenz[b,f]azepin-5-yl)-1-propyl)amino)benzoic acid ethyl ester.

TLC: $R_f$=0.67 ($SiO_2$: ethyl acetate/heptane=1:2).

The above crude ester was dissolved in ethanol (100 ml) and tetrahydrofuran (50 ml), and 4N sodium hydroxide (30 ml) was added. After stirring for 24 h at room temperature the mixture was concentrated in vacuo and the residue was mixed with water (100 ml) and acidified by addition of concentrated hydrochloric acid. The aqueous phase was extracted with dichloromethane (2×30 ml) and the combined extracts were washed with brine (50 ml ). Drying ($MgSO_4$) and concentration in vacuo afforded an oil, which was redissolved in a mixture of ethyl acetate (4.0 ml) and heptane (10 ml). After 12 h, the precipitate was filtered off and dried, affording 0.71 g (41%) of the title compound as crystals.

M.p. 170–172° C. Calculated for $C_{24}H_{24}N_2O_2$: C, 77.40%; H, 6.49%; N, 7.52%; Found: C, 77.26%; H, 6.76%; N, 7.22%.

Example 2

3-((3-(10,11-Dihydro-5H-dibenz[b,f]azepin-5-yl)-1-propyl)amino)propionic Acid Hydrochloride

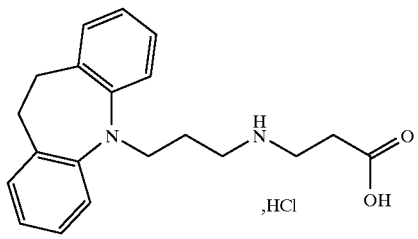

To a suspension of 10,11-dihydro-5H-dibenz[b,f]azepine (15.2 g, 0.078 mol) in toluene (100 ml), 3-chloropropionyl chloride (9.50 ml, 0.099 mol) was added, and the resulting mixture was heated at reflux temperature for 1 h. Saturated aqueous sodium bicarbonate (100 ml) was added, and the phases were separated. The organic phase was washed with brine (100 ml), dried ($MgSO_4$) and concentrated in vacuo. This afforded 23.6 g of 3-chloro-1-(10,11-dihydro-5H-dibenz[b,f]azepin-5-yl)-1-propanone as a solid which was used in the following step without further purification.

M.p. 107–108° C. Calculated for $C_{17}H_{16}ClNO$: C, 71.45%; H, 5.64%; N, 4.90%. Found: C, 71.45%; H, 5.79%; N, 5.01%.

To a solution of the above crude chloride (14.0 g, 0.044 mol) in tetrahydrofuran (150 ml) at 0° C., sodium borohydride (6.66 g, 0.176 mol) was added, followed by dropwise addition of glacial acetic acid (10.0 ml). The resulting mixture was stirred at room temperature overnight and then heated at reflux temperature for 2 h. More sodium borohydride (6.50 g, 172 mmol) and then borontrifluoride diethyl etherate (20.0 ml, 0.163 mol) were added and heating at reflux temperature was continued for 20 h. Water (350 ml) was cautiously added and the phases were separated. The aqueous phase was extracted with toluene (3×100 ml). The combined organic phases were washed with brine (3×100 ml), dried ($MgSO_4$) and concentrated in vacuo. The residue was purified by flash chromatography on silica gel (100 g) using a gradient of heptane and ethyl acetate (10:0→10:2), to give 4.58 g (38%) of 5-(3-chloropropyl)-10,11-dihydro-5H-dibenz[b,f]azepine as an oil.

TLC: $R_f$=0.63 ($SiO_2$: ethyl acetate/heptane=1:2).

β-Alanine ethyl ester hydrochloride (1.52 g, 0.0099 mol) was suspended in acetonitrile (5.0 ml), and diisopropylethylamine (2.41 g, 0.019 mol), a solution of the above chloride (1.72 g, 0.0063 mol) in acetonitrile (5.0 ml) and potassium iodide (0.93 g, 0.0056 mol) were added. The resulting mixture was heated at reflux temperature for 8 h and stirred at room temperature overnight. Water (50 ml) was added and the aqueous phase was extracted with ethyl acetate (3×30 ml). The combined organic extracts were washed with brine (2×20 ml), dried (MgSO$_4$) and concentrated in vacuo. The residue was mixed with water (50 ml) and concentrated hydrochloric acid (3.0 ml), and washed with a mixture of heptane (20 ml) and toluene (20 ml). The organic phase was discarded. The aqueous phase was extracted with a mixture of toluene (20 ml) and dichloromethane (20 ml). The combined organic extracts were dried (MgSO$_4$) and concentrated in vacuo. The product was crystallised by redissolving the residue in a mixture of ethyl acetate (5.0 ml) and heptane (3.0 ml). This afforded after filtration and drying 0.24 g (10%) of 3-((3-(10,11-dihydro-5H-dibenz[b,f]azepin-5-yl)-1-propyl)amino)propionic acid ethyl ester hydrochloride as a powder.

M.p. 111–120° C. Calculated for C$_{22}$H$_{28}$N$_2$O$_2$, HCl: C, 67.94%; H, 7.51%; N, 7.20%. Found: C, 67.57%; H, 7.69%; N, 7.13%.

The above ester hydrochloride (0.20 g, 0.51 mmol) was dissolved in ethanol (2.0 ml) and a solution of sodium hydroxide (0.10 g, 2.50 mmol) in water (0.5 ml) was added. The resulting mixture was stirred at room temperature for 5 h. A mixture of water (20 ml) and concentrated hydrochloric acid (3.0 ml) was added, and the aqueous phase was extracted with dichloromethane (7×15 ml) and dried (MgSO$_4$). Evaporation of the solvent yielded a foam, which was mixed with water (0.5 ml). A solid precipitated, which was filtered off, washed with water (0.5 ml), ethyl acetate (0.5 ml), suspended in toluene (3.0 ml) and concentrated in vacuo, affording 0.12 g (65%) of the title compound as a powder.

M.p. 114–117° C. Calculated for C$_{20}$H$_{24}$N$_2$O$_2$, HCl, H$_2$O: C, 63.40%; H, 7.18%; N, 7.39%. Found: C, 63.46%; H, 7.23%; N, 7.15%.

Example 3

2-((N-(3-(10,11-Dihydro-5H-dibenz[b,f]azepin-5-yl)-1-propyl)-N-methylamino)methyl)benzoic Acid Hydrochloride

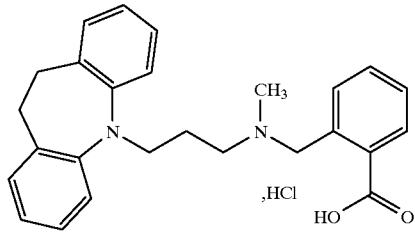

A mixture of 2-methylbenzoic acid ethyl ester (9.87 g, 0.060 mol), carbontetrachloride (75 ml), N-bromosuccinimide (10.7 g, 0.060 mol) and dibenzoyl peroxide (0.62 g, 0.002 mol, containing 25% water) was heated at reflux temperature for 1.5 h. The mixture was then allowed to cool to room temperature and filtered. The filter cake was washed with heptane (2×20 ml) and the combined filtrates were concentrated in vacuo, affording 14.9 g of a liquid, which quickly turned yellow. $^1$H-NMR inspection revealed that the liquid was a mixture of mainly the desired 2-(bromomethyl)benzoic acid ethyl ester and the starting material. This mixture was used in the following reaction without further purification.

A mixture of N-(3-(10,11-dihydro-5H-dibenz[b,f]azepin-5-yl)-1-propyl)-N-methylamine hydrochloride (1.57 g, 0.0052 mol), acetonitrile (20 ml), potassium carbonate (1.51 g, 0.011 mol), lithium bromide (0.23 g, 0.0027 mol) and the above crude bromide (1.30 g, 0.0054 mol) was heated at reflux temperature for 5 h. Water (50 ml) was added and the mixture was extracted with ethyl acetate (2×30 ml). The combined organic extracts were washed with brine (30 ml), dried (MgSO$_4$) and concentrated in vacuo. The product was purified by column chromatography on silica gel (70 g) using a gradient of heptane and ethyl acetate (10:0→10:3). This afforded 1.09 g (49%) of 2-((N-(3-(10,11-dihydro-5H-dibenz[b,f]azepin-5-yl)-1-propyl)-N-methylamino)methyl)-benzoic acid ethyl ester as an oil.

TLC: R$_f$=0.50 (SiO$_2$: ethyl acetate/heptane=1:1).

A mixture of the above ester (0.80 g, 0.0019 mol), ethanol (10 ml), tetrahydrofuran (10 ml) and 4N sodium hydroxide (2 ml) was stirred at room temperature for 72 h. Water (50 ml) and concentrated hydrochloric acid (3 ml) were added and the mixture was extracted with ethyl acetate (2×30 ml). The combined organic extracts were washed with brine (30 ml), dried (MgSO$_4$) and concentrated in vacuo. The residue was triturated with ethyl acetate and dried in vacuo to give 0.71 g (87%) of the title compound as an amorphous foam.

HPLC retention time=24.74 minutes (5 μm C18 4×250 mm column, eluting with a 20–80% gradient of 0.1% trifluoroacetic acid/acetonitrile and 0.1% trifluoroacetic acid/water over 30 minutes at 35° C.). Calculated for C$_{26}$H$_{28}$N$_2$O$_2$, HCl, 1.75 H$_2$O C, 66.66%; H, 6.62%; N, 5.98%; Found: C, 66.80%; H, 6.89%; N, 5.52%.

Example 4

2-(N-(3-(10,11-Dihydro-5H-dibenz[b,f]azepin-5-yl)-1-propyl)-N-methylamino)nicotinic Acid

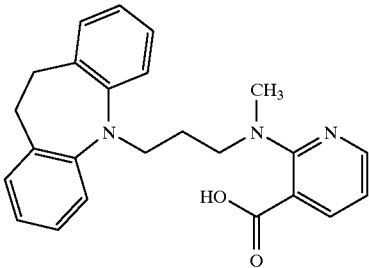

To a solution of diisopropylamine (3.47 9, 0.034 mol) in tetrahydrofuran (100 ml) at −78° C., n-butyllithium (13 ml, 0.033 mol, 2.5M in hexane) was added. The reaction mixture was allowed to warm up to −30° C., and the mixture was then again cooled down to −78° C. Pre-cooled 2-bromopyridine (3.0 ml, 0.032 mol) was slowly added, and when addition was complete, the resulting mixture was stirred at −75° C. for 1 h. Ethyl chloroformate (5.0 ml, 0.052 mol) was added at once and the cooling bath was removed. At −10° C., saturated aqueous sodium bicarbonate (20 ml) was added followed by water (200 ml), and the mixture was extracted with ethyl acetate (3×100 ml). The combined organic extracts were washed with brine (2×100 ml), dried (MgSO$_4$) and concentrated in vacuo. This afforded 9.18 g of an oil, containing crude 2-bromonicotinic acid ethyl ester, which was used without further purification in the following reaction.

A mixture of the above crude ester (9.18 g), N-(3-(10,11-dihydro-5H-dibenz[b,f]azepin-5-yl)-1-propyl)-N- methylamine hydrochloride (8.47 g, 0.028 mol), diisopropylethylamine (10.6 g, 0.082 mol), acetonitrile (10 ml) and potassium iodide (1.70 g, 0.010 mol) was heated at reflux temperature for 28 h. Water (100 ml) was added and the mixture was extracted with ethyl acetate (3×100 ml). The combined organic extracts were washed with brine (100 ml), dried (MgSO$_4$) and concentrated in vacuo. The residue was purified by column chromatography on silica gel (90 g) using a gradient of heptane and ethyl acetate (10:0→10:7), affording 6.63 g (36%) of crude 2-(N-(3-(10,11-dihydro-5H-dibenz[b,f]azepin-5-yl)-1-propyl)-N-methylamino)nicotinic acid ethyl ester as an oil.

TLC: R$_f$=0.74 (SiO$_2$: heptane/ethyl acetate=1:1).

A mixture of the above crude ester (6.60 g), methanol (50 ml), tetrahydrofuran (30 ml) and 4N sodium hydroxide (10 ml) was stirred at room temperature for 24 h, at 65° C. for 9 h and then at room temperature for 48 h. Water (100 ml) and concentrated hydrochloric acid (10 ml) were added and the product was extracted with dichloromethane (3×20 ml). The combined organic extracts were washed with brine (100 ml), dried (MgSO$_4$) and concentrated in vacuo. The residue was purified by column chromatography on silica gel (100 g) using a gradient of heptane and ethyl acetate (1:1→0:1). This afforded 1.93 g (50%) of the title compound as an oil, which crystallised after standing 1 day at room temperature. The product was recrystallised from a mixture of ethyl acetate and heptane to give 1.45 g of the title compound.

TLC: R$_f$=0.32 (SiO$_2$: ethyl acetate). M.p. 133–135° C. Calculated for C$_{24}$H$_{25}$N$_3$O$_2$: C, 74.40%; H, 6.50%; N, 10.84%; Found: C, 74.46%; H, 6.65%; N, 10.70%.

Example 5

3-((3-(10,11-Dihydro-5H-dibenz[b,f]azepin-5-yl)-1-propyl)amino)benzoic Acid

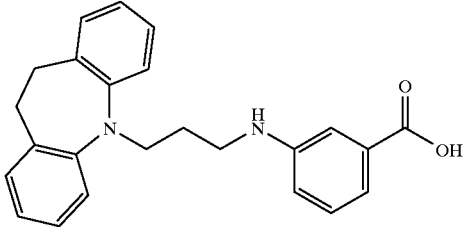

A mixture of 5-(3-chloropropyl)-10,11-dihydro-5H-dibenz[b,f]azepine (1.5 g, 0.0055 mol, prepared similarly as described in example 2) and potassium iodide (5.4 g, 0.0327 mol) in methyl ethyl ketone (100 ml) was heated at reflux temperature for 1 h and then stirred at room temperature overnight. The mixture was filtered and the solvent evaporated in vacuo. The crude halogenide was dissolved in dry dimethyl sulfoxide (15 ml) and kept. A solution of 3-acetylaminobenzoic acid ethyl ester (1.5 g, 7.4 mmol) in dry dimethyl sulfoxide (15 ml) was heated to 50° C. and sodium hydride (0.32 g, 8.1 mmol, 60% oil dispersion) was added in portions. The resulting mixture was heated at 120° C. for 2.5 h, and the mixture was allowed to cool to 80° C. before the above solution containing the halogenide was added. The resulting mixture was heated at 115–120° C. overnight and then allowed to cool to room temperature. Water (100 ml) was added and the resulting mixture was extracted with dichloromethane (3×200 ml). The organic extracts were discarded and pH of the aqueous phase was adjusted to 7. The aqueous phase was extracted with ethyl acetate (100 ml) and dichloromethane (2×100 ml), and the combined organic extracts were dried (MgSO$_4$). The volatiles were removed in vacuo to give a residue which was purified by flash chromatography on silica gel (200 g) using ethyl acetate as eluent, affording 1.0 g of 3-(N-acetyl-N-(3-(10,11-dihydro-5H-dibenz[b,f]azepin-5-yl)-1-propyl)-amino)benzoic acid ethyl ester as an oil.

TLC: R$_f$=0.32 (SiO$_2$: ethyl acetate).

To a solution of the above ester (1.0 g, 0.0023 mol) in ethanol (5 ml), 4N sodium hydroxide (0.6 ml) was added and the mixture was stirred at room temperature for 6 h and then left in a freezer overnight. The reaction mixture was allowed to warm up to room temperature and additional 4N sodium hydroxide (0.6 ml) was added. The mixture was stirred at room temperature for 3 h. Water and 4N hydrochloric acid (1.7 ml) were added, and the mixture was extracted with dichloromethane (2×200 ml). The combined organic extracts were dried (MgSO$_4$) and the solvent was evaporated in vacuo. The residue was stripped twice with dichloromethane and dried in vacuo affording 0.5 g (59%) of the title compound as an amorphous solid.

HPLC retention time=25.4 minutes (5 μm C18 4×250 mm column, eluting with a 20–80% gradient of 0.1% trifluoroacetic acid/acetonitrile and 0.1% trifluoroacetic acid/water over 30 minutes at 35° C.).

$^1$H NMR (400 MHz, CDCl$_3$) δ 1.90 (q, 2H), 3.18 (s, 4H), 3.20 (t, 2H), 3.85 (t, H), 6.71 (dd, 1H), 6.92 (t, 2H), 7.05–7.21 (m, 7H), 7.27 (d, 1H), 7.41 (d, 1H).

Example 6

2-((3-(10,11-Dihydro-5H-dibenzo[a,d]cyclohepten-5-ylidene)-1-propyl)amino)-benzoic Acid

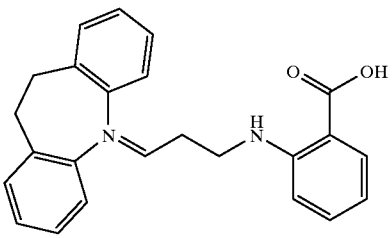

To a suspension of potassium carbonate (8.3 g, 0.06 mol) and potassium iodide (3.3 g, 0.02 mol) in methyl ethyl ketone (100 ml), 2-aminobenzoic acid ethyl ester (2.1 ml, 0.014 mol) and 5-(3-bromo-1-propylidene)-10,11-dihydro-5H-dibenzo[a,d]cycloheptene (3.00 g, 0.0096 mol) were added and the mixture was stirred vigorously at reflux temperature for 12 days. After cooling, water (100 ml) was added and the phases were separated. The aqueous phase was extracted with ethyl acetate (100 ml) and the combined organic extracts were dried (MgSO$_4$) and evaporated in vacuo. The residue was purified by column chromatography on silica gel (800 ml) using a mixture of ethyl acetate and heptane (1:10). This afforded 1.2 g of 2-((3-(10,11-dihydro-5H-dibenzo-[a,d]cyclohepten-5-ylidene)-1-propyl)amino) benzoic acid ethyl ester as an oil.

The above ester (1.2 g) was dissolved in 96% ethanol (20 ml) and 1N sodium hydroxide (10 ml) was added. The mixture was heated at reflux temperature for 3 h and stirred overnight at room temperature. Water (50 ml) and diethyl ether (35 ml) were added. The phases were separated and the aqueous phase was washed with diethyl ether (35 ml). The aqueous phase was treated with 1N hydrochloric acid, and extracted with ethyl acetate (75 ml). The organic phase was dried (MgSO$_4$) and evaporated in vacuo to give 0.36 g of the title compound as a solid.

M.p. 164–167° C. Calculated for C$_{25}$H$_{23}$NO$_2$: C, 81.27%; H, 6.29%; N, 3.79%; Found: C, 80.84%; H, 6.44%; N, 3.65%.

Example 7

5-Bromo-2-(N-(3-(10,11-dihydro-5H-dibenzo[a,d]cyclohepten-5-ylidene)-1-propyl)amino)benzoic Acid

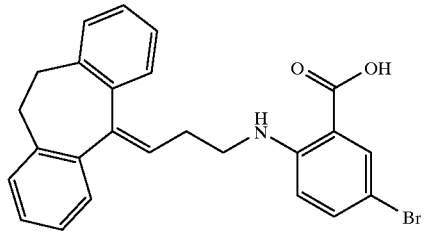

5-(3-Bromo-1-propylidene)-10,11-dihydro-5H-dibenzo[a,d]cycloheptene (6.13 g, 19.6 mmol, prepared as described in WO 9518793), potassium carbonate (10.8 g, 78 mmol), potassium iodide (4.3 g, 26 mmol), and 2-amino-5-bromobenzoic acid methyl ester (3.00 g, 13.0 mmol) were mixed in methyl ethyl ketone (200 ml) and heated at reflux temperature for 17 days. After cooling, the mixture was filtered, and the filtrate was evaporated. The residue was purified by column chromatography on silica gel (800 ml) using a mixture of ethyl acetate and heptane (1:9) as eluent. This afforded 1.14 g of crude 5-bromo-2-(N-(3-(10,11-dihydro-5H-dibenzo[a,d]cyclohepten-5-ylidene)-1-propyl)amino)benzoic acid methyl ester. This was used in the next step without further purification.

TLC: R$_f$=0.44 (SiO$_2$: ethyl acetate/heptane=1:10).

The above crude ester (1.14 g) was dissolved in ethanol (10 ml) and 1N sodium hydroxide (10 ml) was added. The resulting mixture was heated at reflux temperature for 16 h. After cooling, water (150 ml) was added. The resulting mixture was extracted with diethyl ether (2×100 ml), and the organic phases were dried (MgSO$_4$) and evaporated. The resulting crude product was purified by column chromatography on silica gel (200 ml) eluting first with heptane then with a mixture of ethyl acetate, heptane and acetic acid (1:2:0.03) to give 0.47 g (51%) of the title compound.

M.p. 226.5–227.0° C. Calculated for C$_{25}$H$_{22}$BrNO$_2$: C, 66.97%; H, 4.95%; N, 3.12% Found: C, 67.28%; H, 5.01%, N, 2.94%.

$^1$H-NMR (200 MHz, CDCl$_3$+DMSO-d$_6$): δ 2.47 (q, 2H), 2.78 (bd, 2H), 3.00 (bd, 2H), 3.3 (b, 2H), 5.59 (t, 1H), 6.36 (d, 1H), 7.0–7.3 (m, 9H), 7.99 (d, 1H).

Example 8

2-(N-(3-(3-Chloro-10,11-dihydro-5H-dibenz[b,f]azepin-5-yl)-1-propyl)amino)benzoic Acid

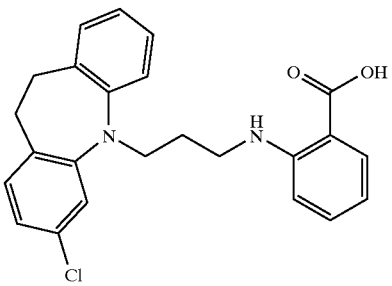

3-Chloro-10,11-dihydro-5H-dibenz[b,f]azepine (3.82 g, 16.6 mmol) was dissolved in toluene (20 ml). A solution of 3-chloropropionylchloride (2.53 g, 19.9 mmol) in toluene was added dropwise, and the resulting mixture was heated to 95° C. and stirred at that temperature for 30 minutes. The mixture was stirred overnight at room temperature. Further 3-chloropropionylchloride (2.53 g, 19.9 mmol) was added and the mixture was stirred at 95° C. for 1.5 h. After cooling, 0.2M sodium hydroxide (10 ml) was added, and the phases were separated. The organic phase was diluted with more toluene (50 ml), and washed with first 0.2M sodium hydroxide (6×10 ml) and then with more 0.2M sodium hydroxide (3×20 ml) until the water phase was alkaline. The organic phase was washed with water (3×15 ml), brine (25 ml), and dried (MgSO$_4$). Evaporation in vacuo afforded 5.23 (98%) crude 3-chloro-1-(3-chloro-10,11-dihydro-5H-dibenz[b,f]azepin-5-yl)-1-propanone as an oil. This was further purified by addition of a mixture of heptane and ethyl acetate (1:1). This afforded 3.14 g (59%) of the product as a solid.

A 1.0M solution of lithiumaluminium hydride in tetrahydrofuran (18.7 ml, 18.7 mmol) was introduced into a 250 ml dry, three-necked, roundbottom flask under a nitrogen atmosphere. The solution was cooled on an icebath. Concentrated sulphuric acid (0.5 ml) was added dropwise, with caution, over 10 minutes. More dry tetrahydrofuran (20 ml) was added to compensate for evaporated solvent and the mixture was stirred for 15 minutes. Additional tetrahydrofuran was added (20 ml) and the icebath was removed. The mixture was stirred for 75 minutes at room temperature. The above amide (3.0 g, 9.3 mmol) was dissolved in dry tetrahydrofuran (25 ml) and dropwise added over 20 minutes. The reaction mixture was stirred for 1 h. Water (0.7 ml) was added, followed subsequently by 4N sodium hydroxide (0.7 ml) and water (2.1 ml). Stirring was continued for 30 minutes. The mixture was filtered (hyflo) and evaporated in vacuo, affording 2.70 g (95%) 3-chloro-5-(3-chloropropyl)-10,11-dihydro-5H-dibenz[b,f]azepine as an oil.

The above chloride (1.0 g, 3.3 mmol) was dissolved in 2-aminobenzoic acid ethyl ester (3.6 ml, 25 mmol), and potassium iodide (0.54 g, 3.3 mmol) was added. The resulting mixture was heated at 110° C. overnight. After cooling, water (40 ml) was added. The aqueous mixture was extracted with ethyl acetate (2×25 ml), and the combined organic phases were washed with brine (25 ml) and dried (MgSO$_4$). After evaporation in vacuo, the crude 2-(N-(3-(3-chloro-10,11-dihydro-5H-dibenz[b,f]azepin-5-yl)-1-propyl)amino)benzoic acid ethyl ester was used directly in the next step.

The above ester was dissolved in a mixture of ethanol (160 ml) and tetrahydrofuran (80 ml). A solution 4M sodium hydroxide (50 ml) was added, and the reaction mixture was stirred at room temperature for 53 h. After evaporation of the solvents, water (150 ml) was added, and the solution was acidified by addition of concentrated hydrochloric acid. The mixture was extracted with dichloromethane (2×50 ml). The combined organic extracts were washed with brine (75 ml), dried (MgSO$_4$) and evaporated in vacuo. The residue was redissolved in acetone (6 ml) and water (20 ml) was added. The resulting precipitate was filtered off and suspended in water (150 ml), and the mixture was stirred overnight. The solid was filtered off and recrystallised in isopropyl acetate. This afforded 0.5 g (37%) of the title compound.

M.p. 176–178° C. Calculated for $C_{24}H_{23}N_2O_2Cl$: C, 70.84%; H, 5.70%; N, 6.88%, Found: C, 70.45%; H, 5.85%; N, 6.65%.

We claim:

1. A compound of formula I

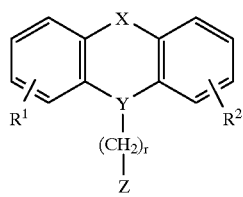

(I)

wherein

R$^1$ and R$^2$ independently are hydrogen, halogen, trifluoromethyl, hydroxy, $C_{1-6}$-alkyl or $C_{1-6}$-alkoxy;

Y is >N—CH$_2$— wherein only the underscored atom participates in the ring system;

X is —CH$_2$CH$_2$—, —CH$_2$—(C═O)— or —(C═O)—CH$_2$—;

r is 1, 2 or 3; and

Z is

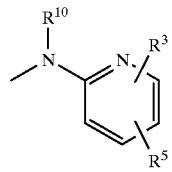

(A)

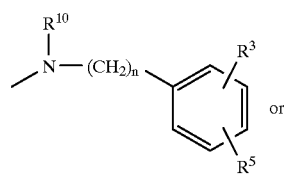

(B)

or

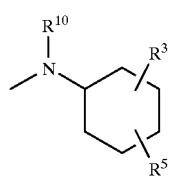

(C)

wherein n is 0 or 1; R$^3$ is —(CH$_2$)$_m$OH or —(CH$_2$)$_s$COR$^4$ wherein m is 0, 1, 2, 3, 4, 5 or 6, s is 0 or 1, and R$^4$ is —OH, —NH$_2$, —NHOH or $C_{1-6}$-alkoxy; R$^5$ is hydrogen, halogen, trifluoromethyl, hydroxy, $C_{1-6}$-alkyl or $C_{1-6}$-alkoxy; R$^{10}$ is hydrogen or $C_{1-6}$-alkyl; A is $C_{1-6}$-alkylene, $C_{2-6}$-alkenylene or $C_{2-6}$-alkynylene; or a pharmaceutically acceptable salt thereof.

2. A compound according to claim 1, wherein X is —CH$_2$—CH$_2$—.

3. A compound according to claim 1 which is:

2-(N-(3-(10,11-Dihydro-5H-dibenz[b,f]azepin-5-yl)-1-propyl)-N-methylamino)succinic acid;

2-((N-(3-(10,11-Dihydro-5H-dibenz[b,f]azepin-5-yl)-1-propyl)-N-methylamino)-1-cyclohexanecarboxylic acid;

2-(3-(10,11-Dihydro-5H-dibenz[b,f]azepin-5-yl)-1-propylamino)pyridin-3-ol;

2-((3-(10,11-Dihydro-5H-dibenz[b,f]azepin-5-yl)-1-propyl)amino)benzoic acid;

2-((N-(3-(10,11-Dihydro-5H-dibenz[b,f]azepin-5-yl)-1-propyl)-N-methylamino)methyl)benzoic acid;

2-(N-(3-(10,11-Dihydro-5H-dibenz[b,f]azepin-5-yl)-1-propyl)-N-methylamino)nicotinic acid;

3-((3-(10,11-Dihydro-5H-dibenz[b,f]azepin-5-yl)-1-propyl)amino)benzoic acid;

2-(N-(3-(3-Chloro-10,11-dihydro-5H-dibenz[b,f]azepin-5-yl)-1-propyl)amino)benzoic acid; or a pharmaceutically acceptable salt thereof.

4. A pharmaceutical composition comprising a compound according to claim 1 together with a pharmaceutically carrier or diluent.

5. The pharmaceutical composition according to claim 4, comprising between 0.5 mg and 1000 mg of the compound per unit dose.

6. A compound of formula I

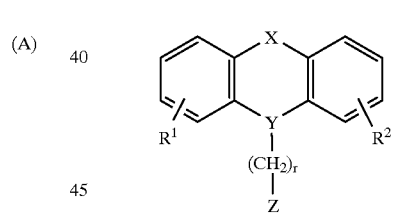

(I)

wherein

R$^1$ and R$^2$ independently are hydrogen, halogen, trifluoromethyl, hydroxy, $C_{1-6}$-alkyl or $C_{1-6}$-alkoxy;

Y is >N—CH$_2$— wherein only the underscored atom participates in the ring system;

X is —CH═CH—;

r is 1, 2 or 3; and

Z is

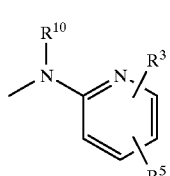

(A)

(B)

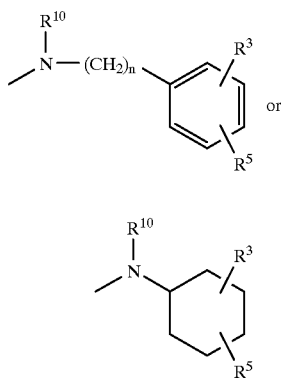

or (C)

wherein n is 0 or 1; $R^3$ is —$(CH_2)_mOH$ or —$(CH_2)_sCOR^4$ wherein m is 0, 1, 2, 3, 4, 5 or 6, s is 0 or 1, and $R^4$ is —OH, —$NH_2$, —NHOH or $C_{1-6}$-alkoxy; $R^5$ is hydrogen, halogen, trifluoromethyl, hydroxy, $C_{1-6}$-alkyl or $C_{1-6}$-alkoxy; $R^{10}$ is hydrogen or $C_{1-6}$-alkyl; A is $C_{1-6}$-alkylene, $C_{2-6}$-alkenylene or $C_{2-6}$-alkynylene; or a pharmaceutically acceptable salt thereof.

7. A pharmaceutical composition comprising a compound according to claim 6 together with a pharmaceutically carrier or diluent.

8. A method of treating insulin resistance, neurogenic inflammation, migraine, diabetic neuropathy or rheumatoid arthritis in a subject in need thereof, comprising administering to the subject a compound of formula I (I)

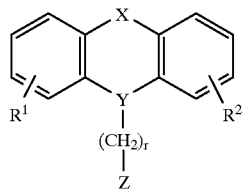

wherein $R^1$ and $R^2$ independently are hydrogen, halogen, trifluoromethyl, hydroxy, $C_{1-6}$-alkyl or $C_{1-6}$-alkoxy;

Y is >N—$CH_2$— wherein only the underscored atom participates in the ring system;

X is —$CH_2CH_2$—, —$CH_2$—(C=O)—, —(C=O)—$CH_2$—, or —CH=CH—;

r is 1, 2 or 3; and

Z is (A)

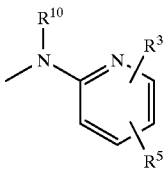

(B)

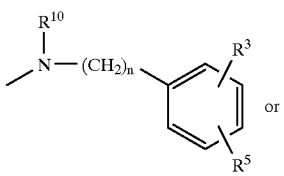

or (C)

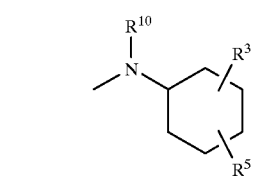

wherein n is 0 or 1; $R^3$ is —$(CH_2)_mOH$ or —$(CH_2)_sCOR^4$ wherein m is 0, 1, 2, 3, 4, 5 or 6, s is 0 or 1, and $R^4$ is —OH, —$NH_2$, —NHOH or $C_{1-6}$-alkoxy; $R^5$ is hydrogen, halogen, trifluoromethyl, hydroxy, $C_{1-6}$-alkyl or $C_{1-6}$-alkoxy; $R^{10}$ is hydrogen or $C_{1-6}$-alkyl; A is $C_{1-6}$-alkylene, $C_{2-6}$-alkenylene or $C_{2-6}$-alkynylene; or a pharmaceutically acceptable salt thereof.

* * * * *